(12) United States Patent
Ashby et al.

(10) Patent No.: US 7,695,492 B1
(45) Date of Patent: Apr. 13, 2010

(54) ENHANCED BLEED BACK SYSTEM

(75) Inventors: Mark Ashby, Launa Niguel, CA (US);
Andrew H. Cragg, Edina, MN (US);
Luis R. Urquidi, Oceanside, CA (US);
Eduardo Chi Sing, Dana Point, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1224 days.

(21) Appl. No.: 10/462,065

(22) Filed: Jun. 12, 2003

Related U.S. Application Data

(63) Continuation-in-part of application No. 09/621,670, filed on Jul. 24, 2000, now Pat. No. 7,625,352, and a continuation-in-part of application No. 10/069,107, filed on Dec. 16, 2002, which is a continuation of application No. PCT/US00/26367, filed on Sep. 25, 2000, now Pat. No. 7,201,725.

(60) Provisional application No. 60/156,007, filed on Sep. 23, 1999.

(51) Int. Cl.
*A61M 5/00* (2006.01)
(52) U.S. Cl. .................. 606/213; 606/108; 604/96.01
(58) Field of Classification Search ......... 606/213–215, 606/228–232, 108, 198; 604/264, 265, 96.01, 604/93.01, 164.04, 506; 128/200.26; 600/564, 600/139
See application file for complete search history.

(56) References Cited

U.S. PATENT DOCUMENTS 581,235 A   4/1897  Kenyon 1,578,517 A   3/1926  Hein
2,086,580 A   7/1937  Shirley (Continued)

FOREIGN PATENT DOCUMENTS

EP   0032826   7/1981

(Continued)

OTHER PUBLICATIONS

Allison, D., et al., "Percutaneous liver biopsy and track embolization with steel coils", Radiology, vol. 169, pp. 261-263, (1998).

(Continued)

*Primary Examiner*—Anhtuan T Nguyen
*Assistant Examiner*—Kathleen Sonnett
(74) *Attorney, Agent, or Firm*—Crompton, Seager & Tufte LLC

(57) ABSTRACT

The present invention provides for an apparatus to locate a blood vessel puncture having a bleed back entrance port near a first end, a bleed back exit port near a second end; and a lumen extending between the bleed back entrance port and the bleed back exit port, wherein said bleed back entrance port has a diameter substantially equal to or greater than the lumen diameter. The present invention further provides for a method for locating a blood vessel puncture by inserting a locator into a blood vessel lumen, the locator having a bleed back entrance port at a first end, a bleed back exit port at a second end, and a finger adjacent the bleed back entrance port, observing a blood flow out of the bleed back exit port, and withdrawing the locator out of the blood vessel lumen until the finger contacts the blood vessel wall.

8 Claims, 10 Drawing Sheets

U.S. PATENT DOCUMENTS

| | | | |
|---|---|---|---|
| 2,465,357 A | 3/1949 | Correll | |
| 2,492,458 A | 12/1949 | Bering, Jr. | |
| 2,507,244 A | 5/1950 | Correll | |
| 2,558,395 A | 6/1951 | Studer | |
| 2,597,011 A | 5/1952 | MacMasters et al. | |
| 2,680,442 A | 6/1954 | Linzmayer | |
| 2,761,446 A | 9/1956 | Reed | |
| 2,814,294 A | 11/1957 | Figge | |
| 2,824,092 A | 2/1958 | Thompson | |
| 2,899,362 A | 8/1959 | Sieger, Jr. et al. | |
| 3,157,524 A | 11/1964 | Artandi | |
| 3,308,819 A * | 3/1967 | Arp | 604/164.04 |
| 3,724,465 A | 4/1973 | Duchane | |
| 4,000,741 A | 1/1977 | Binard et al. | |
| 4,211,323 A | 7/1980 | Olsen | |
| 4,218,155 A | 8/1980 | Weidner | |
| 4,238,480 A | 12/1980 | Sawyer | |
| 4,292,972 A | 10/1981 | Pawelchak | |
| 4,323,072 A | 4/1982 | Rosenbluth et al. | |
| 4,340,066 A | 7/1982 | Shah | |
| 4,390,018 A | 6/1983 | Zuloowski | |
| 4,404,970 A | 9/1983 | Sawyer | |
| 4,515,637 A | 5/1985 | Cioca | |
| 4,583,968 A * | 4/1986 | Mahurkar | 604/43 |
| 4,587,969 A | 5/1986 | Gillis | |
| 4,588,395 A | 5/1986 | Lemelson | |
| 4,619,261 A | 10/1986 | Guerriero | |
| 4,619,913 A | 10/1986 | Luck et al. | |
| 4,645,488 A | 2/1987 | Matukas | |
| 4,675,004 A * | 6/1987 | Hadford et al. | 604/44 |
| 4,698,056 A * | 10/1987 | Ciannella | 604/164.02 |
| 4,708,718 A | 11/1987 | Daniels | |
| 4,744,364 A | 5/1988 | Kensey | |
| 4,790,819 A | 12/1988 | Li et al. | |
| 4,829,994 A | 5/1989 | Kurth | |
| 4,850,960 A | 7/1989 | Grayzel | |
| 4,852,568 A | 8/1989 | Kensey | |
| 4,890,612 A | 1/1990 | Kensey | |
| 4,900,303 A | 2/1990 | Lemelson | |
| 4,929,246 A | 5/1990 | Sinofaky | |
| 4,936,835 A | 6/1990 | Haaga | |
| 4,950,234 A | 8/1990 | Fujioka et al. | |
| 5,007,895 A | 4/1991 | Burnett | |
| 5,021,059 A | 6/1991 | Kensey et al. | |
| 5,049,138 A * | 9/1991 | Chevalier et al. | 604/265 |
| 5,052,998 A * | 10/1991 | Zimmon | 604/8 |
| 5,053,046 A | 10/1991 | Janese | |
| 5,061,274 A | 10/1991 | Kensey | |
| 5,080,655 A | 1/1992 | Haaga | |
| 5,108,421 A | 4/1992 | Fowler | |
| 5,163,904 A | 11/1992 | Lampropoulous et al. | |
| 5,167,624 A | 12/1992 | Butler et al. | |
| 5,192,300 A | 3/1993 | Fowler | |
| 5,192,301 A | 3/1993 | Kamiya et al. | |
| 5,195,988 A | 3/1993 | Haaga | |
| 5,220,926 A | 6/1993 | Jones | |
| 5,221,259 A | 6/1993 | Weldon et al. | |
| 5,224,938 A * | 7/1993 | Fenton, Jr. | 604/247 |
| 5,242,683 A | 9/1993 | Klaveness | |
| 5,275,616 A | 1/1994 | Fowler | |
| 5,282,827 A * | 2/1994 | Kensey et al. | 606/215 |
| 5,304,131 A * | 4/1994 | Paskar | 604/95.04 |
| 5,310,407 A | 5/1994 | Casale | |
| 5,322,515 A | 6/1994 | Karas et al. | |
| 5,325,857 A | 7/1994 | Nabai et al. | |
| 5,334,216 A | 8/1994 | Vidal et al. | |
| 5,360,416 A * | 11/1994 | Ausherman et al. | 604/264 |
| 5,366,480 A | 11/1994 | Corriveau et al. | |
| 5,370,656 A | 12/1994 | Shevel | |
| 5,383,896 A | 1/1995 | Gershony et al. | |
| 5,383,899 A | 1/1995 | Hammersiag | |
| 5,385,550 A | 1/1995 | Su et al. | |
| 5,388,588 A | 2/1995 | Nabai et al. | |
| 5,391,183 A | 2/1995 | Janzen et al. | |
| 5,403,291 A * | 4/1995 | Abrahamson | 604/523 |
| 5,417,699 A | 5/1995 | Klein | |
| 5,419,765 A | 5/1995 | Weldon et al. | |
| 5,431,639 A * | 7/1995 | Shaw | 604/264 |
| 5,437,292 A | 8/1995 | Kipshidze | |
| 5,437,631 A | 8/1995 | Janzen | |
| 5,443,481 A | 8/1995 | Lee | |
| 5,467,780 A | 11/1995 | Nabai et al. | |
| 5,478,352 A | 12/1995 | Fowler | |
| 5,479,936 A | 1/1996 | Nabai et al. | |
| 5,486,195 A | 1/1996 | Myers | |
| 5,490,736 A | 2/1996 | Haber | |
| 5,522,840 A | 6/1996 | Krajicek | |
| 5,522,850 A | 6/1996 | Yomtov et al. | |
| 5,526,822 A | 6/1996 | Burbank et al. | |
| 5,527,332 A | 6/1996 | Clement | |
| 5,529,577 A | 6/1996 | Hammershiag | |
| 5,540,715 A | 7/1996 | Katseros et al. | |
| 5,542,914 A | 8/1996 | Van Iten | |
| 5,545,178 A | 8/1996 | Kensey et al. | |
| 5,558,853 A | 9/1996 | Quay | |
| 5,591,204 A | 1/1997 | Janzen et al. | |
| 5,591,205 A | 1/1997 | Fowler | |
| 5,601,602 A | 2/1997 | Fowler | |
| 5,601,603 A | 2/1997 | Illi | |
| 5,645,566 A | 7/1997 | Brennenman et al. | |
| 5,649,547 A | 7/1997 | Ritchart et al. | |
| 5,653,730 A | 8/1997 | Hammersiag | |
| 5,665,107 A | 9/1997 | Hammersiag | |
| 5,676,689 A | 10/1997 | Kensey | |
| 5,681,279 A | 10/1997 | Roper et al. | |
| 5,716,375 A | 2/1998 | Fowler | |
| 5,725,498 A | 3/1998 | Janzen et al. | |
| 5,728,132 A | 3/1998 | Van Tassel et al. | |
| 5,741,223 A | 4/1998 | Janzen et al. | |
| 5,769,086 A | 6/1998 | Ritchart et al. | |
| 5,775,333 A | 7/1998 | Burbank et al. | |
| 5,782,861 A | 7/1998 | Cragg et al. | |
| 5,800,389 A | 9/1998 | Burney et al. | |
| 5,810,806 A | 9/1998 | Ritchart et al. | |
| 5,830,130 A | 11/1998 | Janzen et al. | |
| 5,858,008 A | 1/1999 | Capaccio | |
| 5,868,762 A | 2/1999 | Cragg et al. | |
| 5,902,310 A | 5/1999 | Foerster et al. | |
| 5,984,950 A | 11/1999 | Cragg et al. | |
| 6,007,563 A | 12/1999 | Nash et al. | |
| 6,027,471 A | 2/2000 | Fallon et al. | |
| 6,027,482 A | 2/2000 | Imbert | |
| 6,027,514 A * | 2/2000 | Stine et al. | 606/159 |
| 6,071,300 A | 6/2000 | Brenneman et al. | |
| 6,071,301 A | 6/2000 | Cragg et al. | |
| 6,086,607 A | 7/2000 | Cragg et al. | |
| 6,161,034 A | 12/2000 | Burbank et al. | |
| 6,162,192 A | 12/2000 | Cragg et al. | |
| 6,183,497 B1 | 2/2001 | Sing et al. | |
| 6,200,328 B1 | 3/2001 | Cragg et al. | |
| 6,293,958 B1 * | 9/2001 | Berry et al. | 606/191 |
| 6,315,753 B1 | 11/2001 | Cragg et al. | |
| 6,709,408 B2 * | 3/2004 | Fisher | 600/570 |
| 6,767,339 B2 * | 7/2004 | Reydel | 604/175 |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637431 | 11/1994 |
| FR | 2641692 | 7/1990 |
| GB | 1509023 | 4/1978 |
| GB | 1569660 | 6/1980 |

| | | |
|---|---|---|
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 96/08208 | 3/1996 |
| WO | WO 96/24290 | 8/1996 |
| WO | WO 98/06346 | 2/1998 |
| WO | WO 98/40016 | 9/1998 |
| WO | WO 99/56692 | 11/1999 |
| WO | WO 99/66834 | 12/1999 |

OTHER PUBLICATIONS

J. Bryne Review Article: Endovascular treatments for intracranial anuerysms, 1996 The British journal of radiology; 98,891-899.
Chuang, V., et al., "Sheath needle for liver biopsy in high-risk patience", Radiology, vol. 166, pp. 261-262 (1988).
John T. Correll, et al., A new Physiologically absorbable sponge.
John T. Correll, et al. Biologic investigations of new absorbable sponge; p. 585.
Fandrich, C., et al. "Small guage gelfoam plug liver biopsy in high risk patients", Australian Radiology, vol. 40, pp. 230-234 (1996).
Foran, JPM, et al. "Early mobilisation after percutaneous cardiac catheterisation using collagen plug (vasoseal) maemostatis" BRHeart, vol. 69, pp. 424-429 (1993).
Gibbs, JSR, "Femoral arterial hemostasis" J. Interventional card, vol. 5, pp. 85-88 (1992).
Journal of interventional cardiology vol. 5 No. 2 Jun.
Kassell, et al. Size of Intracanial aneurysm; vol. 12, No. 3, (1983).
Kiemeneiji, F, et al., "Improved anticoagulation management after Palmaz Schatz coronary stent implantation by sealing the arterial puncture site with vascular hemostasis device", Catheterization and Cardiovascular diagnosis, vol. 30, pp. 1685-1692 (1995).
Kussmaul, WG, "Rapid arterial hemostasis", J. Am. Coll. Card., vol. 25, pp. 1685-1692 (1995).
Pharmacia & Upjohn manufacturer brochure gelfoam sterile sponge, sterile powder and sterile film, pp. 1-34 (May 1997).
Pharmacia & Upjohn manufacturer brochure "gelfoam sterile powder", (Feb. 1996).
Pharmacia & Upjohn manufacturer brochure, "gelfoam sterile powder" (Mar. 1996).
Pharmacia & Upjohn manufacturer brochure (Sep. 1996).
Pharmacia & Upjohn manufacturer specification, "Gelfoam sterile sponge, sterile powder and sterile film" pp. 1-23 (Nov. 1996).
Riley, SA, Percutaneous liver biopsy with plugging of needle track: a safe method for use in patients with impaired coagulation, The lancet, p. 436 (1964).
Sanborn, T. Multicenter randomized trial comparing perutaneous collagen hemostasis device with conventional manual compression after diagnostic angiography and angioplasty, J. Am. Coll. Card., vol. 22, pp. 1273-1279, (1993).
Schievink, et al. The new england journal of medicaine; review articles; intracanial aneurysms; Jan. 2, 1997.
Scharader, R. "Collagen appl.", Catheterization & cardiovascular diagnosis (1992) pp. 298-302.
Silber, S., "Rapid hemostasis of arterial puncture sites with collagen in patients undergoing diagnostic interventional cardiac catheterization", clinical cardiology, vol. 20, pp. 981-992, (1997).
Smith, T., "Percutaneous transhepatic liver biopsy with tract embolization", Radiology, vol. 198, pp. 769-774 (1996).
Szikora, et al. Combined Use of stents and cells to treat experimental wide-necked carotid aneuryms: Preliminary results; AJNR AM newradiol 15: 1091-1102, Jun. 1994.
Szikora, et al. Endovascular treatment of experimental anuerysms with liquid polymers: vol. 38, No. 2, Feb. 1996.
Turjman, et al. Combined stent implantation & endosacular coil placement for tretment of experimental wide-necked aneurysms:AJNRAM J. Neuroradio 15: 1087-1090 Jun. 1994.
Yoshimoto, et al cerebral anuerysms unrelated to arterial bifurcations; Acta neurochir (Wien) (96) 138: 958-964.
Zins, M., "US-guided percutaneous liver biopsy with plugging of the needle track" radiology, vol. 187, pp. 841-843, (1992).

* cited by examiner

ENHANCED BLEED BACK SYSTEM

CROSS-REFERENCE TO RELATED APPLICATIONS

This application is a continuation-in-part of, and claims priority under 35 U.S.C. §120 to, and incorporates by reference herein in their entirety: 1. U.S. patent application Ser. No. 09/621,670 filed Jul. 24, 2000 by inventors Mark Ashby, Andrew Cragg, Luis Urquidi, Eduardo Chi Sing, and Eric Lee entitled "Depth and puncture control for system for hemostatis of blood vessel", now U.S. Pat. Nos. 7,625,352 and 2. U.S. patent application Ser. No. 10/069,107 filed Dec. 16, 2002 by inventors Mark Ashby, Rodney Brenneman, Andrew Cragg, and Eduardo Chi Sing entitled "Device and Method for Determining a Depth of an Incision", now Issued U.S. Pat. No. 7,201,725, which was a national stage filing of International Application No. PCT/US00/26367, filed Sep. 25, 2000, and which is the non-provisional application of provisional application Ser. No. 60/156,007 filed Sep. 23, 1999.

FIELD OF THE INVENTION

The present invention relates to locating a blood vessel puncture. More particularly, the present invention relates to locating a blood vessel puncture using an enhanced visual bleed back system.

BACKGROUND OF THE INVENTION

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface but may be unsuitable for patients with substantial amounts of subcutaneous adipose tissue since the skin surface may be a considerable distance from the vascular puncture site.

There are several prior art devices that try to overcome the disadvantages of the traditional external pressure application. For example, there are devices that place a hemostat within the bloodstream of the vessel, within the wall of the blood vessel, or adjacent to the wall of the blood vessel puncture site to close the puncture. However, reliance is on tactile sensation alone to indicate to the surgeon the proper placement of the puncture closing instrumentation. Other prior art references require a separate device for locating the blood vessel puncture site which is must then be removed for insertion of a second device to expel a hemostat. Still other prior art devices use bleed back ports to locate the blood vessel puncture site in conjunction with other devices such as a foot plate placed against the blood vessel wall or closure devices with anchors. However, in some of these prior art devices a surgeon is then required to use sutures and/or needles to close the blood vessel puncture. Moreover, in some of the prior art devices, external pressure applied at the surface of the skin may still be required.

Other devices utilize a dilator having a bleed back entrance port and a bleed back exit port. However, current dilators used today, as shown in FIG. 6, require the blood to traverse through a long, narrow, and often restricted lumen before exiting the bleed back exit port. This results in poor visual bleed back, which compromises the accuracy of the blood vessel puncture site as further discussed below with reference to FIG. 6. Moreover, since the blood must traverse through a long and thin lumen, the blood may quickly and easily clot further restricting the blood flow out of the bleed back exit port.

Thus, there is still a need for an apparatus and method to efficiently and easily locate a blood vessel puncture site.

BRIEF DESCRIPTION OF THE INVENTION

The present invention provides for an apparatus to locate a blood vessel puncture having a bleed back entrance port near a first end, a bleed back exit port near a second end; and a lumen extending between the bleed back entrance port and the bleed back exit port, wherein said bleed back entrance port has a diameter substantially equal to or greater than the lumen diameter. The present invention further provides for a method for locating a blood vessel puncture by inserting a locator into a blood vessel lumen, the locator having a bleed back entrance port at a first end, a bleed back exit port at a second end, and a finger adjacent the bleed back entrance port, observing a blood flow out of the bleed back exit port, and withdrawing the locator out of the blood vessel lumen until the finger contacts the blood vessel wall.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings.

DETAILED DESCRIPTION

Embodiments of the present invention are described herein in the context of an enhanced bleed back system. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1A:
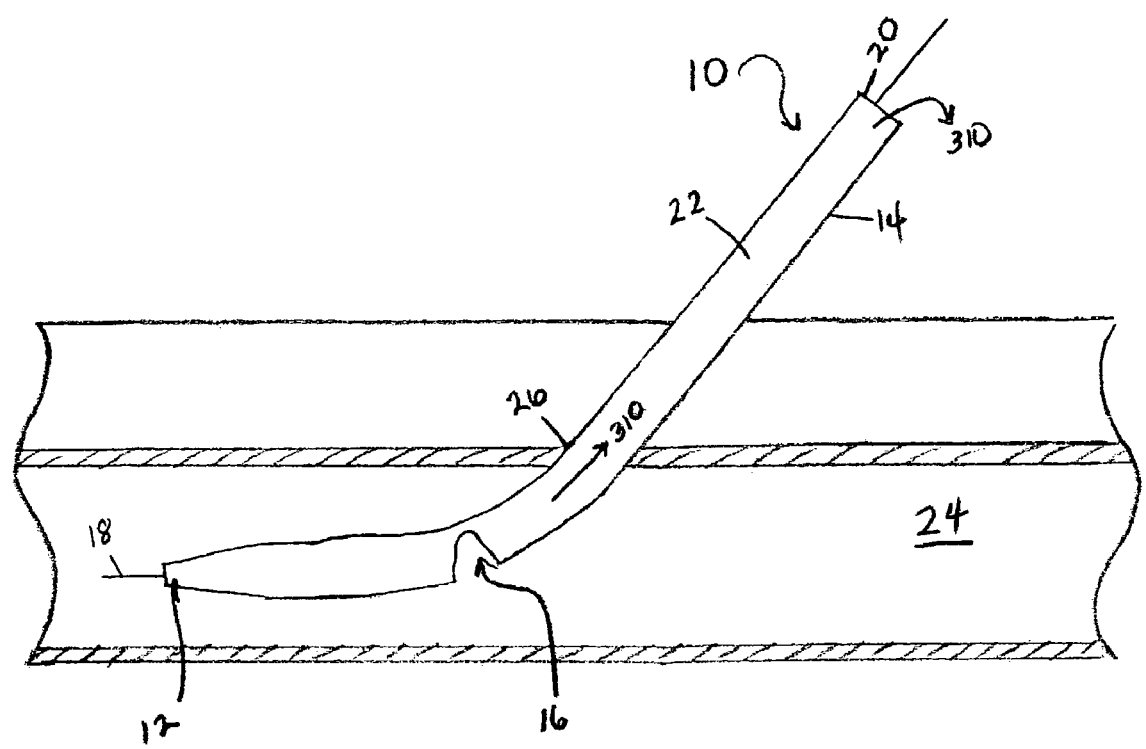
FIGS. 1A and 1B illustrate an apparatus to locate a blood vessel puncture site in accordance with one embodiment of the present invention.
Figure 1B:
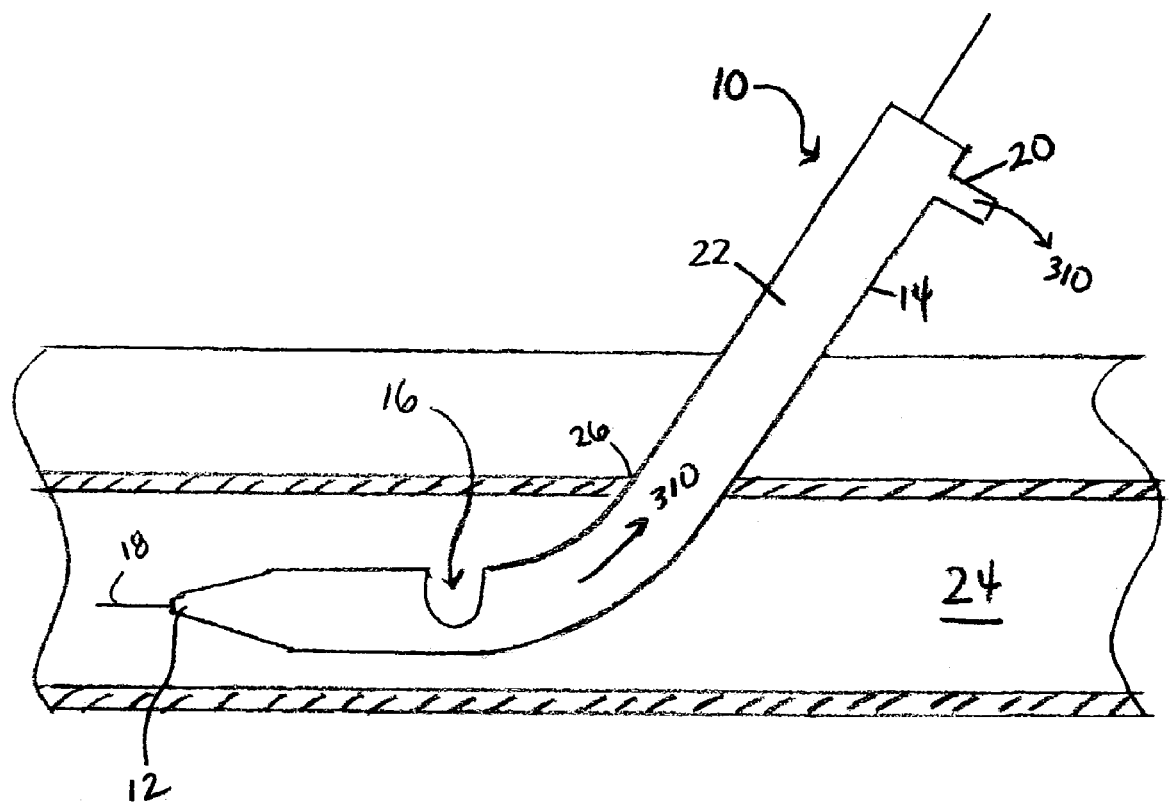

Precisely locating an artery is important for procedures such as puncture closure. Thus, the present invention is directed to a method and apparatus to accurately locate a blood vessel puncture site. Referring now to FIGS. 1A and 1B, the apparatus, generally numbered as 10, has a first end 12, a second end 14, a bleed back entrance port 16 and a bleed back exit port 20. A flash tube lumen 22 extends between the bleed back entrance port 16 and the bleed back exit port 20.

The bleed back entrance port may be located away from the blood vessel puncture 26 or on the bottom surface of the apparatus 10 as shown in FIG. 1A or may be located toward the blood vessel puncture 26 or on the top surface of the apparatus 10 as shown in FIG. 1B. The bleed back exit port 20 may be any exit port that allows for visual indication of bleed back such as a side tube 20 near the second end 14 as shown in FIG. 1B or may be an opening 20 at the second end 14 as shown in FIG. 1A.

Figure 2A:
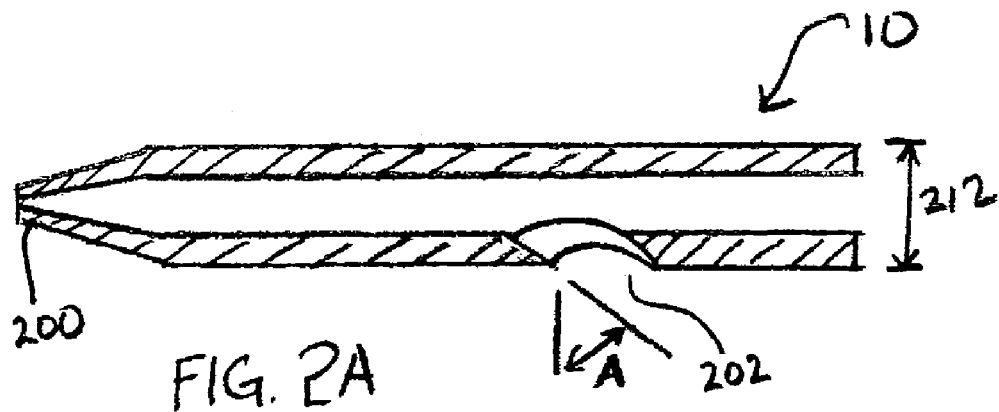
FIGS. 2A, 2B, and 2C illustrate embodiments of the bleed back entrance port.
Figure 2B:
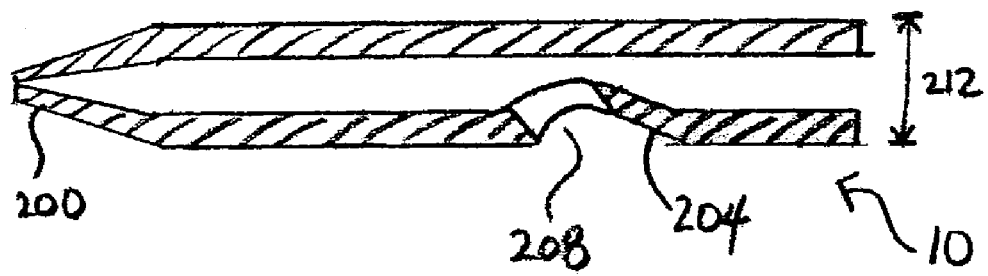
Figure 2C:
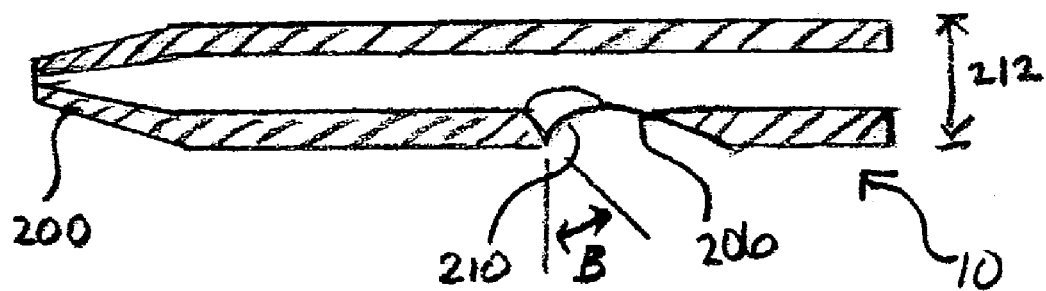

FIGS. 2A, 2B, and 2C illustrate embodiments of the bleed back entrance port. The bleed back entrance port 202, 208, and 210 are openings having a diameter substantially equal to or greater than the flash tube lumen diameter 212. This creates a large hole for a greater amount of blood to flow into the flash tube lumen to provide for a stronger and accurate visual bleed back indication out of the bleed back exit port. FIG. 2A illustrates the bleed back entrance port 202 created at an angle A, where A is greater than or equal to 0°. FIG. 2B illustrates the bleed back entrance port 208 located near a recess 204. FIG. 2C illustrates the bleed back entrance port 210 created at an angle B, where B is greater than 0°, such that a recess 206 is also formed in the outer surface 212 of the apparatus 10 from the same cut as the bleed back entrance port 210.

Figure 3:
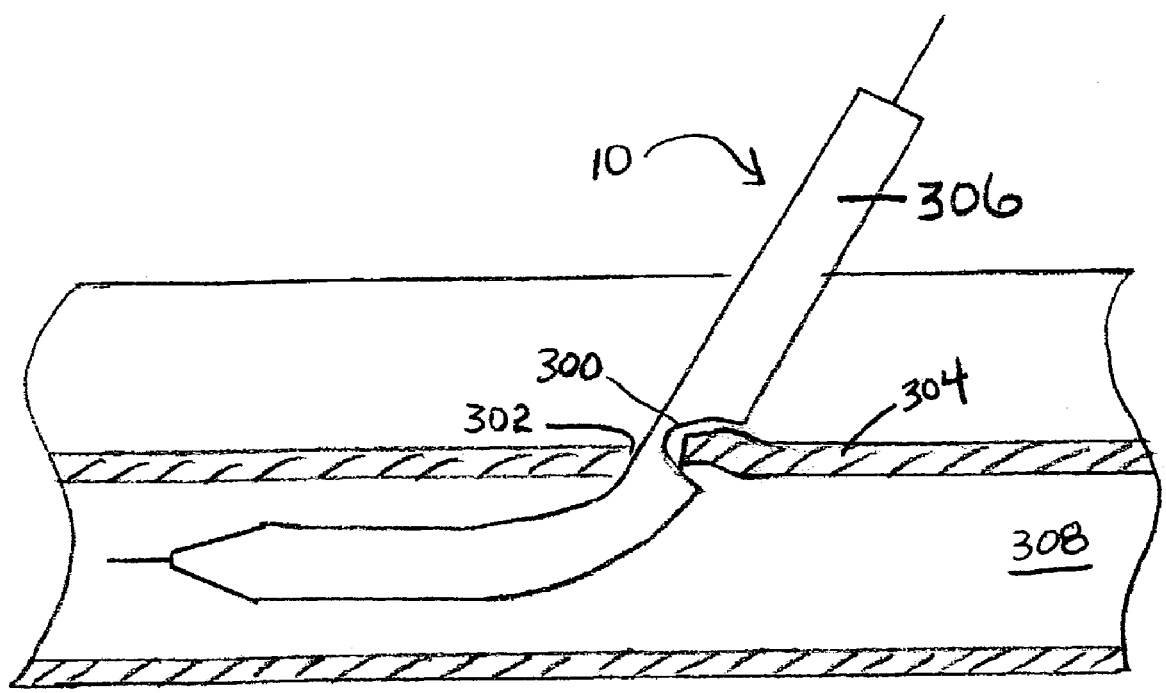
FIG. 3 illustrates the apparatus engaged on a blood vessel wall.

FIG. 3 illustrates the apparatus 10 at a blood vessel puncture site 302. Once the apparatus 10 is inserted into the blood vessel lumen 24 (shown in FIGS. 1A and 1B), blood will flow into the bleed back entrance port 16 in the direction of arrow 310 and out the bleed back exit port 20. This informs a user that the apparatus 10 is inside the blood vessel lumen 24. As the apparatus 10 is pulled out of the blood vessel lumen 308, as shown in FIG. 3, the bleed back entrance port 300 engages the blood vessel wall 304. Since the bleed back entrance port 300 has a diameter greater than or equal to the diameter of the flash tube lumen 306, it creates a flexible region that is able to engage the blood vessel wall 304 and provide tension to resist withdraw of the apparatus 10. The recesses 204 or 206 illustrated in FIG. 2B or 2C further assist and provide for the ability of the bleed back entrance port 300 to interact with the blood vessel wall 304 by providing a niche for the blood vessel wall 304 to enter the bleed back entrance port 300. Once the bleed back entrance port 300 engages the blood vessel wall 304, the apparatus 10 provides for bleed back control and informs the user of the accurate location of the blood vessel puncture site 302 through both the visual confirmation of less or no bleed back and by tactile resistance to withdrawal the apparatus.

Figure 4A:
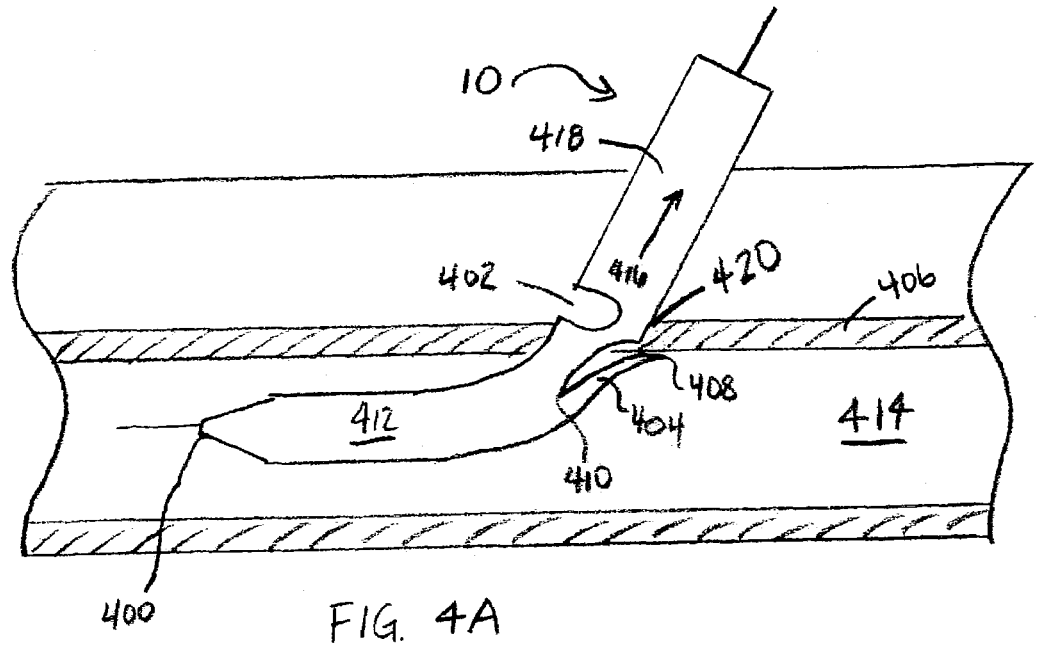
FIGS. 4A, 4B, and 4C illustrate an apparatus to locate a blood vessel puncture site in accordance with another embodiment of the present invention.
Figure 4B:
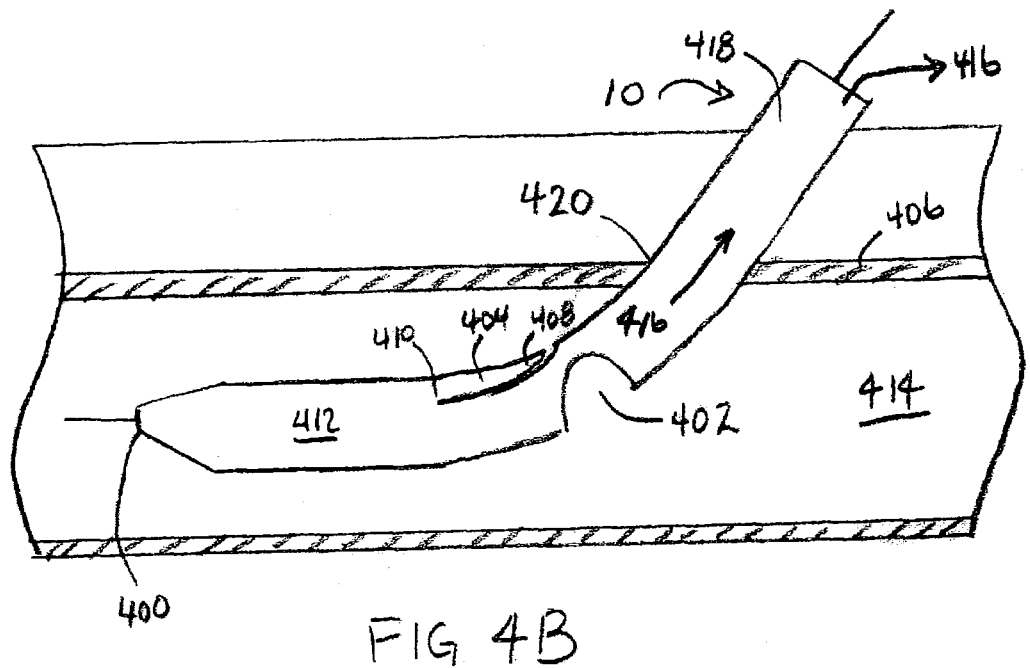
Figure 4C:
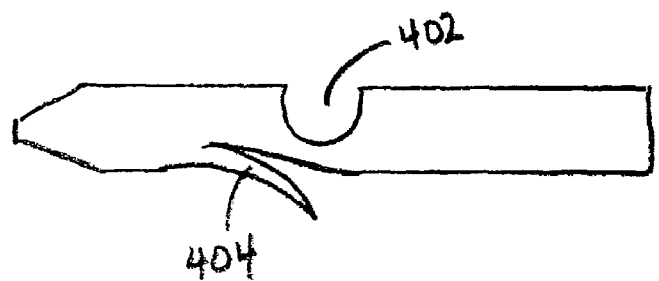

FIGS. 4A, 4B, and 4C illustrate an apparatus to locate a blood vessel puncture site in accordance with another embodiment of the present invention. To further assist the apparatus 10 in engaging the blood vessel wall 406, the apparatus 10 may include a finger 404. The finger 404 is a recess or cut in the apparatus 10. It is preferable that the finger 404 be oriented downward toward the first end 400 and located substantially close to the bleed back entrance port 402. As shown in FIG. 4A, the finger origin 408 may be located near the center of the bleed back entrance port 402 and the finger termination 410 may be located substantially adjacent the bleed back entrance port 402 but toward the first end 400. However, the location of the finger 404 is not meant to be limiting. Those of ordinary skill in the art will now appreciate that the finger 404 may be placed in any position that will allow for the apparatus to engage the blood vessel wall 406.

Moreover, the finger 404 may be made to have a closed position as shown in FIG. 4B when the bottom end 412 is straight. Alternatively, as shown in FIG. 4C, the finger 404 may be configured to be normally biased open. The finger 404 may also be biased closed by the inward radial force applied by tissue in the tissue tract during advancement of the apparatus in the tissue tract or by inward radial force applied by a sleeve, guide, or sheath used to advance the apparatus in the tissue tract.

From the closed position, the finger 404 may extend radially outward, as shown in FIG. 4A, when the bottom end 412 is bent. This occurs as the user withdraws the apparatus 10 from the blood vessel lumen 414. As the user withdraws the apparatus 10, the bottom end 412 curves or bends which causes the finger 404 to extend radially outward. Since the blood vessel entrance port 402 is a flexible region, it contributes and exaggerates the amount of local bending and helps to further bias the finger 404 radially outward.

To locate the blood vessel puncture 420, the apparatus 10 is placed within the blood vessel lumen 414. When the bleed back entrance port 402 enters the blood vessel lumen 414, blood will flow through the flash tube 418 in the direction of arrow 416 and out a bleed back exit port. The apparatus 10 is then withdrawn out of the blood vessel lumen 414. As the apparatus 10 is withdrawn and the bleed back entrance port 402 exits the blood vessel lumen 414, visual bleed back out of the bleed back exit port stops or lessens. At approximately the time when the bleed back entrance port 402 exits the blood vessel lumen 414, the finger 404 begins to engage the blood vessel wall 406. Additional tension applied to withdraw the apparatus 10 results in additional engagement and resistance by the finger 404.

It should be appreciated that the bleed back entrance port and finger each provide a benefit independently of each other and may be utilized separately in separate inventions. However, when combined as in the present invention shown in FIG. 4A, 4B, or 4C, they are synergistic. Thus, the combination of the bleed back entrance port and finger is not meant to be a limiting factor of the present invention.

Figure 5:
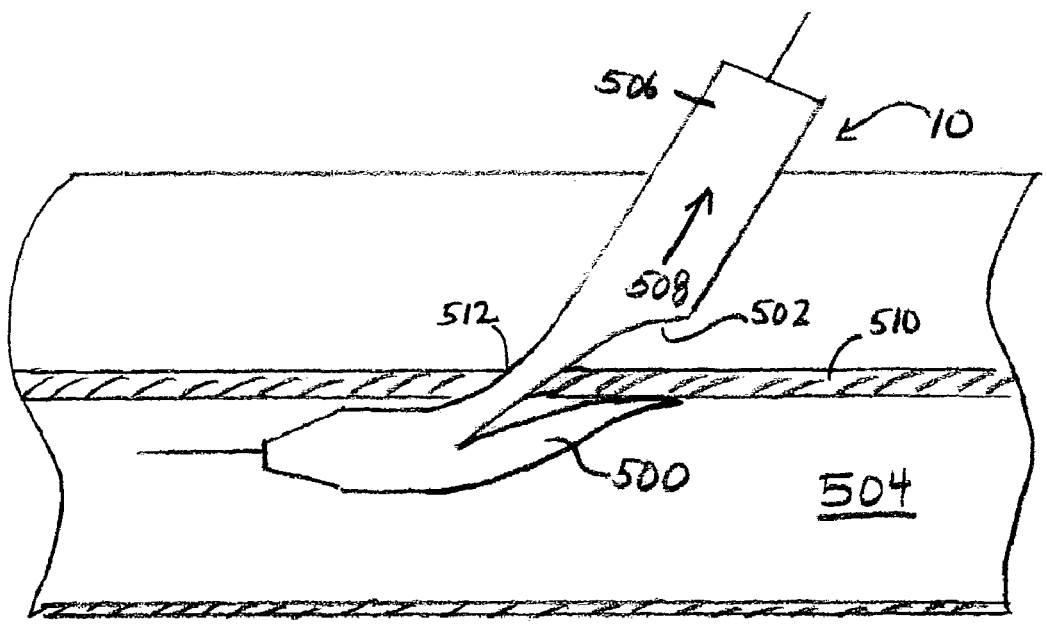
FIG. 5 illustrates an apparatus to locate a blood vessel puncture site in accordance with yet another embodiment of the present invention.

FIG. 5 illustrates an apparatus to locate a blood vessel puncture site in accordance with yet another embodiment of the present invention. The bleed back entrance port 502 and the finger 500 may be formed by the same cut or notch in the apparatus 10. When the apparatus 10 is inserted into the blood vessel lumen 504 and the bleed back entrance port 502 enters the blood vessel lumen 504, blood flows out the flash tube 506 in the direction of arrow 508 and bleed back is observed out of a bleed back exit port. As the apparatus 10 is withdrawn out of the blood vessel lumen 504, the finger 500 may be biased open to engage the blood vessel wall 510. Bleed back out of the bleed back exit port will stop or slow and tension applied when withdrawing the apparatus will increase thereby indicating that the blood vessel puncture 512 is located.

Figure 6:
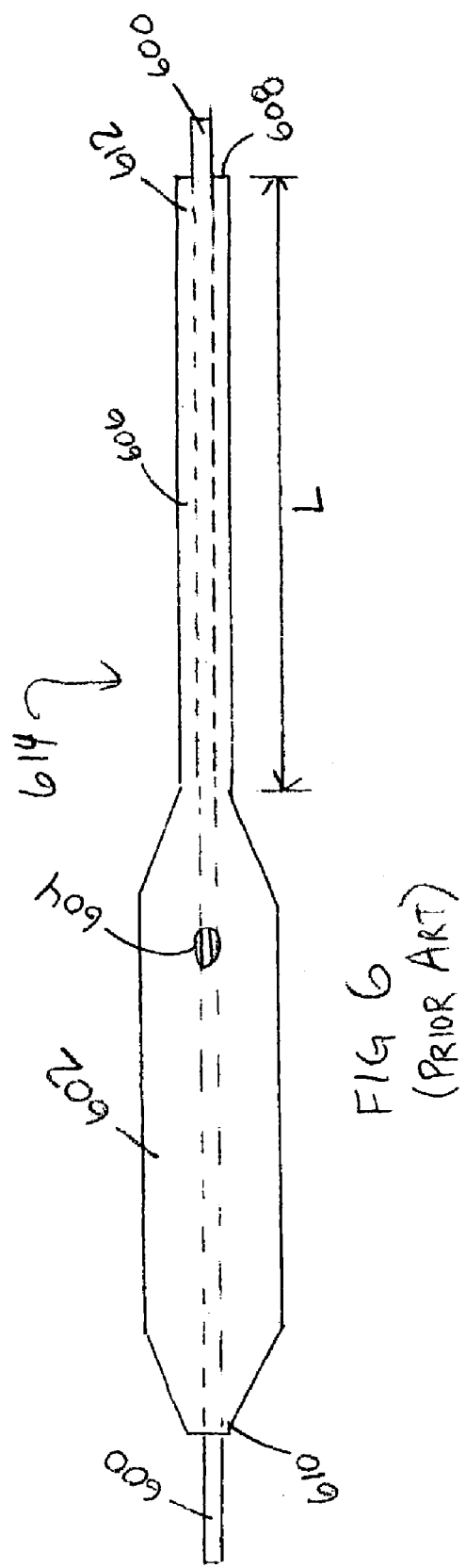
FIG. 6 illustrates an apparatus to locate a blood vessel puncture site.

FIG. 6 illustrates an apparatus to locate a blood vessel puncture site that is currently used and discussed in detail in co-pending patent application Ser. No. 09/621,670. The apparatus 614 has a guidewire 600 extending through the apparatus 614, control tip 602, a bleed back entrance port 604, and a flash tube 606 having length L. When the bleed back entrance port 604 is located within a blood vessel lumen, blood enters the bleed back entrance port 604 and continues through the flash tube 606 and out a bleed back exit port 608. The bleed back exit port may be any exit port that allows for visual indication of bleed back such as the side tube 20 as shown in FIG. 1B or may be an opening 608 at the second end 612 as shown in FIG. 6.

Bleed back through the flash tube 606 that has a guidewire 600 residing within the flash tube 606 is often difficult to read when it exits the bleed back exit port 608. The guidewire 600 occupies a significant percentage of the available flash tube lumen 606 space which decreases the pressure out of the bleed back exit port 608. This causes a significantly less dramatic outflow of blood from the bleed back exit port 608. The result is an outflow of blood that appears like an ooze typically seen when the first end 610 of the apparatus enters the blood vessel lumen rather than a pulsatile appearance. Thus, a user is unable to determine whether the bleed back entrance port 604 is located within the blood vessel lumen which may result in an inaccurate determination of the location of the blood vessel puncture.

Figure 7A:
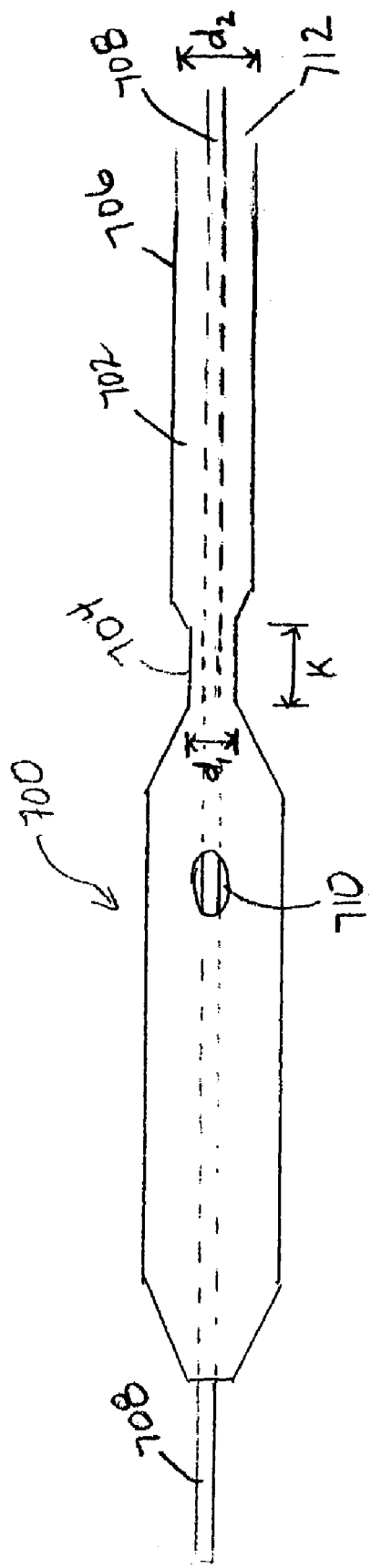
FIGS. 7A and 7B illustrate an apparatus to locate a blood vessel puncture site having an enlarged lumen in accordance to one embodiment of the present invention.
Figure 7B:
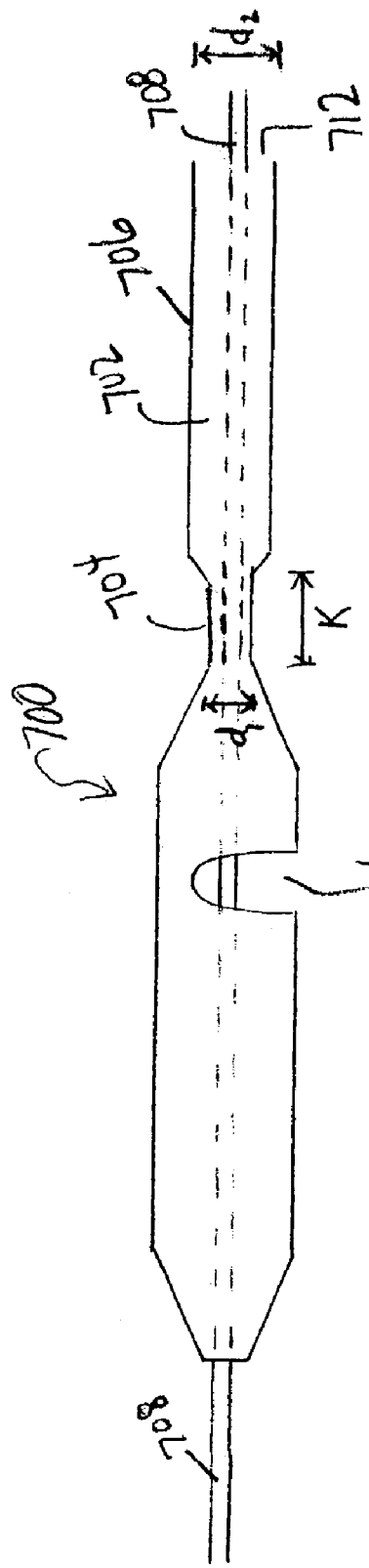

To correct for the disadvantage of the apparatus currently used, FIGS. 7A and 7B illustrate an apparatus to locate a blood vessel puncture site having an enlarged lumen in accordance to one embodiment of the present invention. FIG. 7A shows the device 700 having a flash tube 702 with a bottom portion 704 having a length K and a diameter $d_1$, a top portion 706 having a diameter $d_2$, and a guidewire 708 through the length of the apparatus 700. Diameter $d_2$ is larger than diameter $d_1$, which creates an increased amount of space for blood to flow through the flash tube 702 in the top portion 706. Moreover, length K is as small as possible to minimize the length of the flash tube 702 having a limited area for blood to flow through. The result is less of a pressure drop between the bleed back entrance port 710 to the bleed back exit port 712. As such, the resulting pressure out of the bleed back exit port is greater and visual bleed back out of the bleed back exit port 712 is more dramatic and easily read. FIG. 7B illustrates the apparatus 700 having a bleed back entrance port 714 as disclosed in FIGS. 1A and 1B. Those of ordinary skill in the art will now appreciate that the bleed back entrance port and finger as disclosed above may also be used in the present invention.

Figure 8A:
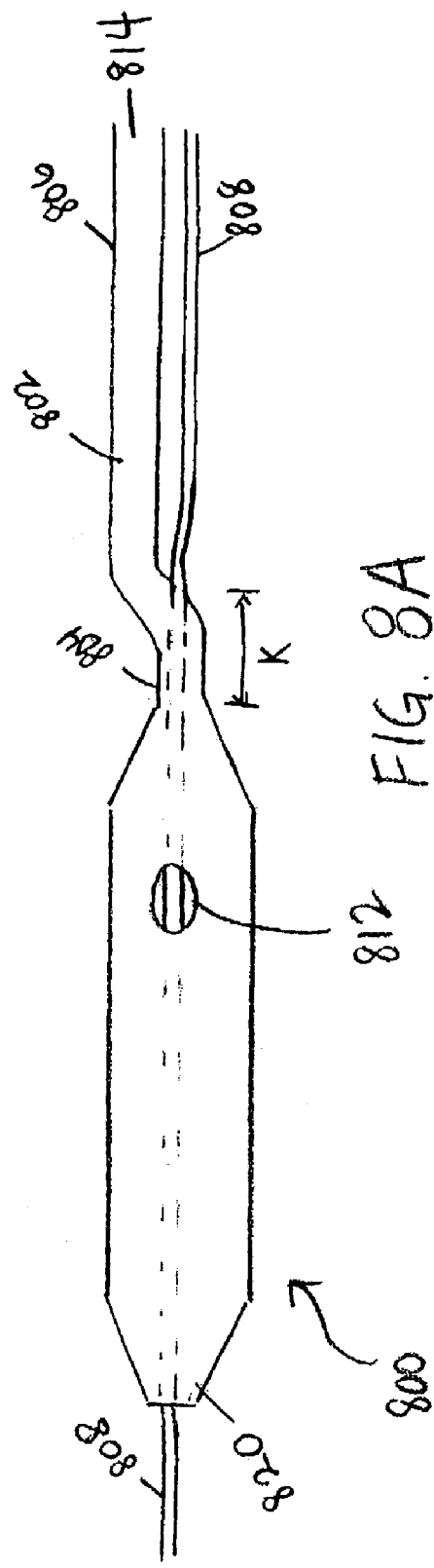
FIGS. 8A and 8B illustrate an apparatus to locate a blood vessel puncture site in accordance with another embodiment of the present invention.
Figure 8B:
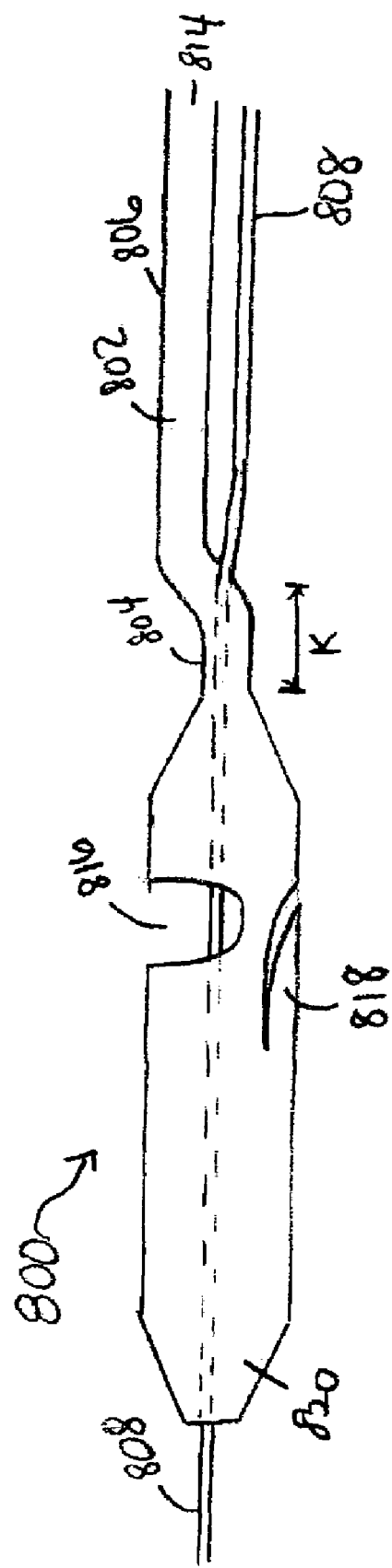

FIGS. 8A and 8B illustrate an apparatus to locate a blood vessel puncture site in accordance with another embodiment of the present invention. The apparatus 800 in FIG. 8A has a flash tube 802 with a bottom portion 804 having a length K, a top portion 806, and a guidewire 808 that extends from the first end 820 and out the bottom portion 804 of the flash tube 802. Thus, the guidewire 808 only extends for length K in the flash tube and does not extend through the top portion 806 of the flash tube 802. This results in even less of a pressure drop between the bleed back entrance port 812 to bleed back exit port 814. As such, visual bleed back out of the bleed back exit port 814 is more dramatic and more easily readable. FIG. 5B illustrates the apparatus 800 having a bleed back entrance port 816 and finger 818 as disclosed in FIGS. 4A, 4B, and 4C. Those of ordinary skill in the art will now appreciate that the bleed back entrance port and finger as disclosed above may also be used with the present invention.

Each of the embodiments described above are discussed with the use of a guidewire to assist in guiding the apparatus through the tissue tract and into the blood vessel lumen. However, the guidewire is not meant to be a limiting factor and may not be required.

Additionally, the first end of each embodiment may be made of any material that is dissolvable when positioned within the blood vessel puncture. Examples of such materials may include those made of absorbable polymers such as Collagen, Oxidized Cellulose, PGA, methyl cellulose, carboxymethyl cellulose, carbowaxes, gelatin (particularly pigskin gelatin), and sugar based compounds. Among the other suitable polymers are polylactic glycolic acids, polyvinyl pyrrolidone, polyvinyl alcohol, polyproline, and polyethylene oxide.

While embodiments and applications of this invention have been shown and described, it would be apparent to those skilled in the art having the benefit of this disclosure that many more modifications than mentioned above are possible without departing from the inventive cOncepts herein. The invention, therefore, is not to be restricted except in the spirit of the appended claims.

What is claimed is:

1. An apparatus to locate a blood vessel puncture, comprising:
    an elongate member having first and second ends, the first end being substantially closed;
    a bleed back entrance port formed near the first end;
    a bleed back exit port formed near the second end;
    a lumen extending through the elongate member between said bleed back entrance port and said bleed back exit port, wherein said bleed back entrance port has a diameter substantially equal to or greater than a lumen diameter to form a flexible region in the elongate member adjacent the bleed back entrance port; and
    a finger positioned substantially opposite the bleed back entrance port and adapted to selectively extend radially outwardly from an exterior surface of the elongate member, the finger including a finger origin located near a center of the bleed back entrance port and a finger termination located substantially adjacent the bleed back entrance port and oriented toward the first end;
    wherein the elongate member comprises a recess area adjacent the bleed back entrance port defining a niche configured to assist insertion of a wall of the blood vessel into the bleed back entrance port.

2. The apparatus of claim 1 wherein said bleed back entrance port is positioned on a top surface of said apparatus.

3. The apparatus of claim 1 wherein said bleed back entrance port is positioned on a bottom surface of said apparatus.

4. The apparatus of claim 1 further comprising a guidewire extending out of said first end and second end.

5. The apparatus of claim 1 wherein said lumen further comprises a bottom portion and a top portion.

6. The apparatus of claim 5 wherein said top portion has a diameter greater than said bottom portion.

7. The apparatus of claim 5 wherein a length of said bottom portion is substantially less than a length of said top portion.

8. The apparatus of claim 5 further comprising a guidewire extending out of said first end and said bottom portion.

* * * * *